United States Patent
Herr

(10) Patent No.: US 11,419,849 B1
(45) Date of Patent: Aug. 23, 2022

(54) METHODS AND PRODUCTS FOR ADVERSE EFFECTS OF AIR TRAVEL, JET LAG, OR A CHANGE TO A SLEEP WAKE TIMING CYCLE

(71) Applicant: Kitt Bio, Inc., Culver City, CA (US)

(72) Inventor: Andrew Herr, Pacific Palisades, CA (US)

(73) Assignee: KITT BIO, INC., Culver City, CA (US)

( * ) Notice: Subject to any disclaimer, the term of this patent is extended or adjusted under 35 U.S.C. 154(b) by 0 days.

(21) Appl. No.: 16/782,966

(22) Filed: Feb. 5, 2020

Related U.S. Application Data

(60) Provisional application No. 62/802,208, filed on Feb. 6, 2019.

(51) Int. Cl.

| | |
|---|---|
| *A61K 31/375* | (2006.01) |
| *A61K 38/06* | (2006.01) |
| *A61K 31/353* | (2006.01) |
| *A61K 31/4745* | (2006.01) |
| *A61K 33/12* | (2006.01) |
| *A61K 31/4415* | (2006.01) |
| *A61K 31/202* | (2006.01) |

(52) U.S. Cl.
CPC .......... *A61K 31/375* (2013.01); *A61K 31/202* (2013.01); *A61K 31/353* (2013.01); *A61K 31/4415* (2013.01); *A61K 31/4745* (2013.01); *A61K 33/12* (2013.01); *A61K 38/063* (2013.01)

(58) Field of Classification Search
CPC ................ A61K 31/375; A61K 38/063; A61K 31/4415; A61K 31/4745; A61K 31/202; A61K 31/353
See application file for complete search history.

(56) References Cited

U.S. PATENT DOCUMENTS

| | | | |
|---|---|---|---|
| 6,436,984 B1 | 8/2002 | Ducrocq et al. | |
| 6,627,732 B1 | 9/2003 | Sakon et al. | |
| 6,794,407 B2 | 9/2004 | Lewy et al. | |
| 8,273,380 B1 * | 9/2012 | Gall-Krasnick | A61K 31/07 424/639 |
| 9,550,744 B2 | 1/2017 | Sloan | |
| 2006/0106437 A1 * | 5/2006 | Czeisler | A61M 21/02 607/88 |
| 2007/0149509 A1 * | 6/2007 | Barella | A61K 31/355 514/221 |
| 2007/0298133 A1 * | 12/2007 | Velazquez | A61P 25/20 514/415 |
| 2009/0054371 A1 | 2/2009 | Goerne | |
| 2014/0308691 A1 | 10/2014 | Weber et al. | |
| 2015/0037308 A1 | 2/2015 | Ikemoto et al. | |
| 2015/0306072 A1 | 10/2015 | Rosa et al. | |

FOREIGN PATENT DOCUMENTS

WO   WO-2009005354 A1 *  1/2009  ........... A23L 33/105

OTHER PUBLICATIONS

Herxheimer et al., BMJ, 2003;326:296-7 (Year: 2003).*
Thakkar et al., European Journal of Clinical Nutrition, 2015;69:1-2 (Year: 2015).*
Pierard et al., Eur J Appl Physiol, 2001;85:144-150 (Year: 2001).*
Wilking, et al., Circadian Rhythm Connections to Oxidative Stress: Implications for Human Health, Antioxidants & Redox Signaling vol. 19, No. 2, 2013, 17 Pages.
Wright, et al., Influence of sleep deprivation and circadian misalignment on cortisol, inflammatory markers, and cytokine balance, Brain, Behavior, and Immunity 47 (2015) 24-34, 11 Pages.
The Science of Jet Lag, Timeshifter, https://www.timeshifter.com/the-science-of-jet-lag, Copyright 2016-2021, accessed Jan. 26, 2021, 5 pages.
Thom, et al., Association of microparticles and neutrophil activation with decompression sickness, J Appl Physiol 119:427-434, 2015, 8 Pages.
Vavricka, et al., High altitude journeys and flights are associated with an increased risk of flares in inflammatory bowel disease patients, Journal of Crohn's and Colitis (2014) 8, 191-199, 9 Pages.
Vinson, et al., Comparative Bioavailability to Humans of Ascorbic Acid Alone or in Citrus Extract, American Journal of Clinical Nutrition vol. 48, No. 3, pp. 601-604, Sep. 1988, 7 Pages.
Wehrens, et al., Meal Timing Regulates the Human Circadian System, 2017, Current Biology 27, 1768-1775, 13 Pages.
Melatonin for Jet Lag, Timeshifter, https://www.timeshifter.com/institute/resources/melatonin-for-jet-lag-type-dose-timing, Copyright 2016-2021, accessed Jan. 26, 2021, 4 pages.
Jet Lag is History, Timeshifter, https://www.timeshifter.com, Copyright 2019, Accessed Jan. 30, 2020, 9 pages.
Link, et al. Methylcobalamin vs. Cyanocobalamin: What's the Difference?, https://www.healthline.com/nutrition/methylcobalamin-vs-cyanocobalamin#bottom-line, Written May 11, 2020, Accessed Feb. 1, 2021, 15 Pages.
My Flight Pack, https://myflightpack.com/shop, Accessed Feb. 1, 2021, 7 Pages.
How It Works, https://myflightpack.com/how-it-works/ Accessed Feb. 1, 2021, 4 Pages.
The Jet lag Reset, https://effectdoctors.com/product/the-jet-lag-reset/, Accessed Feb. 1, 2021, 3 Pages.
Balsalobre, Resetting of Circadian Time in Peripheral Tissues by Glucocorticoid Signaling, Science, New Series, vol. 289, No. 5488 (Sep. 29, 2000), pp. 2344-2347, 5 Pages.

(Continued)

*Primary Examiner* — San Ming R Hui
(74) *Attorney, Agent, or Firm* — Foley & Lardner LLP

(57) ABSTRACT

Methods and products are provided for preventing or reducing adverse effects of air travel, jet lag, and shift switching. Doses of antioxidant, anti-inflammatory, mitochondrial support, circadian shift support, and/or other agents are administered to or by the subject at selected times, and the subject sleeps or refrains from sleep, and/or is exposed to or protected from light, for selected times.

40 Claims, No Drawings

(56) References Cited

OTHER PUBLICATIONS

Bass et al., Circadian Integration of Metabolism and Energetics, Science, New Series, vol. 330, No. 6009 (Dec. 3, 2010), pp. 1349-1354, 7 Pages.

Bearden, et al., Oxidative stress during a 3.5 hour exposure to 120 kPa(a) PO2 in human divers, Undersea and Hyperbaric Medical Society, inc. 1999, 6 Pages.

Bell, Recovery facilitation with Montmorency cherries following high-intensity, metabolically challenging exercise, Appl. Physiol. Nutr. Metab. 40: 414-423 (2015), 11 Pages.

Bishehsari, et al., Alcohol and Gut-Derived Inflammation, Alcohol Research: Current Reviews, vol. 38, No. 2, 10 Pages.

Brown, et al., Melatonin and its relevance to jet lag, Travel Medicine and Infectious Disease (2009) 7, 69e81, 13 Pages.

Burke, et al., Effects of caffeine on the human circadian clock in vivo and in vitro, Sci Transl Med 7, vol. 7 Issue 305, Sep. 15, 2015, 10 Pages.

Caffiene and Travel, Timeshifter, https://www.timeshifter.com/institute/resources/caffeine-and-travel, Copyright 2016-2021, accessed Jan. 26, 2021, 3 pages.

Cajochen, Alerting Effects of Light, Sleep Medicine Reviews (2007) 11, 453-464, 12 Pages.

Cajochen, et al., Evening exposure to a light-emitting diodes (LED)-backlit computer screen affects circadian physiology and cognitive performance, J Appl Physiol 110: 1432-1438, 2011, 7 Pages.

Eastman et al., Advancing Circadian Rhythms Before Eastward Flight: A Strategy to Prevent or Reduce Jet Lag, Sleep. Jan. 1, 2005; 28(1): 33-44, 23 Pages.

Circadian Rhythms and Immune Function, Timeshifter, https://www.timeshifter.com/institute/resources/circadian-rhythms-and-immune-function, Copyright 2016-2021, accessed Jan. 26, 2021, 8 pages.

Damiola, et al., Restricted feeding uncouples circadian oscillators in peripheral tissuesfrom the central pacemaker in the suprachiasmatic nucleus, Genes & Development 14:2950-2961, 2000, 12 Pages.

Dang, et al., Insulin post-transcriptionally modulates Bmal1 protein to affect the hepatic circadian clock, Nat. Commun. 7:12696, (2016), 12 Pages.

Davenne et al., Reliability of simulator driving tool for evaluation of sleepiness, fatigue and driving performance, Accident Analysis and Prevention 45 (2012) 677-682, 6 Pages.

Ebrecht et al., Perceived stress and cortisol levels predict speed of wound healing in healthy male adults, Psychoneuroendocrinology (2004) 29, 798-809, 12 Pages.

Facer-Childs, et al., The Impact of Circadian Phenotype and Time since Awakening on Diurnal Performance in Athletes, Current Biology 25, 518-522 Feb. 16, 2015, 6 Pages.

Fight Jet Lag with Rocket Science, Timeshifter, https://www.timeshifter.com/institute/resources/fight-jet-lag-with-rocket-science, Copyright 2016-2021, accessed Jan. 26, 2021, 9 pages.

Fisman, Fatigue Increases the Risk of Injury From Sharp Devices in Medical Trainees: Results From a Case-Crossover Study, Infection Control and Hospital Epidemiology, vol. 28, No. 1 (Jan. 2007), pp. 10-17, 9 Pages.

For Business, Timeshifter, https://www.timeshifter.com/the-jet-lag-app/business, Copyright 2016-2021, accessed Jan. 26, 2021, 8 pages.

Forsyth, et al., Circadian rhythms, alcohol and gut interactions, Alcohol 49 (2015) 389-398, 11 Pages.

Galgani, et al., Acute effect of meal glycemic index and glycemic load on blood glucose and insulin responses in humans, Nutrition Journal 2006, 5:22, Sep. 5, 2006, 7 Pages.

Gavish, et al., Air travel and the risk of thromboembolism, Intern Emerg Med (2011) 6:113-116, 4 Pages.

Giles, et al., Omega-3 fatty acids and stress-induced changes to mood and cognition in healthy individuals, Pharmacology, Biochemistry and Behavior 132 (2015) 10-19, 10 Pages.

Groeger, et al., Effects of Sleep Inertia After Daytime Naps Vary With Executive Load and Time of Day, Behavioral Neuroscience, 2011, vol. 125, No. 2, 252-260, 9 Pages.

Hart, How Sugar Tunes Your Clock, Cell Metabolism 17, Feb. 5, 2013, 2 Pages.

Hashimoto, et al., Vitamin B12 enhances the phase-response of circadian melatonin rhythm to a single bright light exposure in humans, NeuroscienceLetters220 (1996) 129-132, 4 Pages.

Hemilä et al., Vitamin C for preventing and treating the common cold (Review), 2013 The Cochrane Collaboration. Published by John Wiley & Sons, Ltd., 96 Pages.

Johnson, Mitigating Sleep Loss: Assessment of Omega-3 fatty acids, Report from Advanced Brain Monitoring, Inc. 2011, 33 Pages.

Jouris, et al., The effect of omega-3 fatty acid supplementation on the inflammatory response to eccentric strength exercise, Journal of Sports Science and Medicine (2011) 10, 432-438, 7 Pages.

Keane, et al., Effects of Montmorency tart cherry (*Prunus cerasus* L.) consumption on vascular function in men with early hypertension, Am J Clin Nutr 2016;103:1531-9, 9 Pages.

Kolla, et al., Jet lag and shift work sleep disorders: How to help reset the internal clock, Cleveland Clinic Journal of Medicine vol. 78 • No. 10 Oct. 2011, 10 Pages.

Konturek, Gut Clock: Implication of Circadian Rhythms in the Gastointestinal Tract, Journal of Physiology and Pharmacology 2011, 62, 2, 139-150, 12 Pages.

Levine, Vitamin C pharmacokinetics in healthy volunteers: Evidence for a recommended dietary allowance, Proc. Natl. Acad. Sci. USA vol. 93, pp. 3704-3709, Apr. 1996, 6 Pages.

Matsumoto, Orally Administered Delphinidin 3-Rutinoside and Cyanidin 3-Rutinoside Are Directly Absorbed in Rats and Humans and Appear in the Blood as the Intact Forms, J. Agric. Food Chem. 2001, 49, 1546-1551, 6 Pages.

Mayer, et al., Effects of Vitamin B12 on Performance and Circadian Rhythm in Normal Subjects, Neuropsychopharmacology 1996, vol. 15, No. 5, pp. 456-464, 9 Pages.

Milner, et al., Benefits of napping in healthy adults: impact of nap length, time of day, age, and experience with napping, J. Sleep Res. (2009) 18, 272-281, 10 Pages.

Moran-Ramos, et al., When to eat? The influence of circadian rhythms on metabolic health: are animal studies providing the evidence?, Nutrition Research Reviews (2016), 29, 180-193, 14 Pages.

Neilsen, et al., Magnesium supplementation improves indicators of low magnesium status and inflammatory stress in adults older than 51 years with poor quality sleep, Magnesium Research, vol. 23, No. 4, Dec. 2010, 11 Pages.

Obad, et al., The effects of acute oral antioxidants on diving-induced alterations in human cardiovascular function, J Physiol 578.3 (2007) pp. 859-870, 12 Pages.

Padayatty, Vitamin C Pharmacokinetics: Implications for Oral and Intravenous Use, Ann Intern Med. 2004;140:533-537, 6 Pages.

Potter, et al., Nutrition and the circadian system, British Journal of Nutrition (2016), 116, 434-442, 9 Pages.

Reynolds, et al., Sleepy, circadian disrupted and sick: Could intestinal microbiota play an important role in shift worker health?, Molecular Metabolism 6 (2017) 12-13, 4 Pages.

Sack, The pathophysiology of jet lag, Travel Medicine and Infectious Disease (2009) 7, 102-110, 9 Pages.

Shafiee, et al., Defining conditions that lead to the retention of water: The importance of the arterial sodium concentration, Kidney International, vol. 67 (2005), pp. 613-621, 9 Pages.

Smith, et al., Night Shift Performance is Improved by a Compromise Circadian Phase Position: Study 3. Circadian Phase after 7 Night Shifts with an Intervening Weekend Off, Sleep, vol. 31, No. 12, 2008, 7 Pages.

Smith, et al., Practical Interventions to Promote Circadian Adaptation to Permanent Night Shift Work: Study 4, Journal of Biological Rhythms, vol. 24 No. 2, Apr. 2009 161-172, 12 Pages.

Smith, Phase advancing the human circadian clock with blue-enriched polychromatic light, Sleep Medicine 10 (2009) 287-294, 8 Pages.

(56) References Cited

OTHER PUBLICATIONS

Tharion, Caffeine Effects on Marksmanship During High-Stress Military Training with 72 Hour Sleep Deprivation, Aviation, Space, and Environmental Medicine • vol. 74, No. 4 • Apr. 2003, 6 Pages.

* cited by examiner

METHODS AND PRODUCTS FOR ADVERSE EFFECTS OF AIR TRAVEL, JET LAG, OR A CHANGE TO A SLEEP WAKE TIMING CYCLE

FIELD OF THE INVENTION

The present disclosure relates to adverse effects of air travel, jet lag, or a change to a sleep wake timing cycle and to methods and products for preventing or reducing such effects.

BACKGROUND OF THE INVENTION

Several methods and products have been suggested for preventing or reducing jet lag, however none have been generally established as effective.

Faber WO2009005354 discusses a method for suppressing the effects of jet lag on air passengers. The method comprises the steps of A) retrieving personal information of an air traveler, this information comprising at least the identity; B) retrieving flight information comprising at least the location and local times of the departure and arrival locations; C) subsequently formulating on the basis of this information a personal food package for use during the period of travel, with the proviso that the personal food package comprises a number of meals which are provided at regular intervals during the time of travel, wherein the meals are divided into a number of meal types defined by the presence therein of a number of essential food components, wherein the time at which a meal type is served is chosen subject to the local time at the place of destination.

Lewy et al. U.S. Pat. No. 6,794,407 discusses a method for treating circadian rhythm phase disorders, specifically to advance or delay the phase of certain circadian rhythms in humans. The disclosed methods relate to the administration of melatonin at times determined with relation to the time of dim light endogenous melatonin onset. Embodiments capable of alleviating the effects of jet lag, winter depression and shift-work sleep disturbance are said to be provided.

Gall-Krasnick U.S. Pat. No. 8,273,380 discusses a beverage for minimizing or reducing jet lag symptoms which preferably includes vitamin B3, vitamin B5, vitamin B6, vitamin B12, vitamin D, zinc, calcium, iodine, magnesium, manganese, *ginseng, Ginkgo biloba,* grape seed extract, *Echinacea* extract and water. A method for minimizing or reducing jet lag symptoms includes ingestion of the beverage by a traveler, one hour prior to a flight, and/or during the flight, and/or after a flight.

In addition, it is widely understood that individuals feel malaise and other adverse effects after flying, regardless of difference in time zone between origination and destination, with lay people attributing these to a wide variety of factors, including the stress of travel and dry air in planes.

There continues to be an unmet need for effective ways to alleviate or minimize adverse effects of air travel, including but not limited to jet lag.

SUMMARY OF THE INVENTION

The present invention provides methods and products for preventing or reducing one or more adverse effects of air travel, of jet lag, and/or of change to a person's sleep-wake timing cycle, such as from shift switching. The beneficial use of various agents and actions are described for each of the conditions, with particular agents, actions, and combinations thereof being especially beneficial for one or more of the conditions. As disclosed in more detail below, the present methods and products can comprise one or more antioxidant agents, such as an agent selected from the group consisting of Vitamin C, Vitamin E, Glutathione, Flavan-3-ols, and combinations thereof. The present methods and products can comprise one or more anti-inflammatory agents, such as an agent selected from the group consisting of Omega-3 fatty acids, Flavan-3-ols, Magnesium, and combinations thereof. The present methods and products can comprise one or more mitochondrial support agents, such as an agent selected from the group consisting of Ketone Salts or Esters, Medium Chain Triglycerides, CoQ10, PQQ, Vitamin B6, and combinations thereof. The present methods and products can comprise one or more circadian shift support agents, such as an agent selected from the group consisting of Vitamin B12, Vitamin B12 and exposure or intentional increase of exposure to light, Melatonin, Caffeine, Sugar, Light, protection from light (such as with glasses), actions according to a Program as described herein, and combinations thereof. The descriptions of classes of agents (e.g., as antioxidant, anti-inflammatory, etc.) is for convenience of identification and is not intended to require or limit the recited agents to a specific function or activity. Moreover, some agents (such as Flavan-3-ols) may fall within more than one class. For the conditions, using one or more agent from each of the classes is likely to be sufficient or better than sufficient to prevent or reduce the adverse effects.

For preventing or reducing one or more adverse effects of air travel, in some embodiments, the methods and products comprise:
    an antioxidant agent and an anti-inflammatory agent, or
        an antioxidant agent and a mitochondrial support agent, or an antioxidant agent, an anti-inflammatory agent, and a mitochondrial support agent.

For preventing or reducing one or more adverse effects of jet lag, in some embodiments, the methods and products comprise:
    an antioxidant agent, an anti-inflammatory agent, and a circadian shift support agent; or
    an anti-inflammatory agent, a mitochondrial support agent, and a circadian shift support agent; or
    an antioxidant agent, an anti-inflammatory agent, a mitochondrial support agent, and a circadian shift support agent.

For preventing or reducing one or more adverse effects of change to a person's sleep wake (or sleep-wake) timing cycle, in some embodiments, the methods and products comprise:
    an anti-inflammatory agent, and a circadian shift support agent; or a
    mitochondrial support agent, and a circadian shift support agent; or
    an anti-inflammatory agent, a mitochondrial support agent, and a circadian shift support agent.

As an exemplary aspect of the present invention, methods and products are provided for preventing or reducing one or more adverse effects of air travel in a human subject. The methods and products comprising the following steps to or by the subject: administering a dose of Vitamin C or another antioxidant agent between about one and about five hours before commencing air travel; and administering a dose of omega-3 fatty acids or another anti-inflammatory agent between about one and about three hours before commencing said air travel. The methods and products can also comprise administering one or more additional doses of omega-3 fatty acid during a day of said air travel, and/or administering a dose of Vitamin E to the subject between about one and about five hours before commencing said air travel; and/or one or more additional doses of Vitamin E during a day of said air travel. In some embodiments, the methods and products can be employed when said air travel results in the subject changing time zones by at least two, 3, 4, 5, 6, 7, 8, 9, 10, 11, 12, 13, 14, 15, 16, 17, 18, 19, 20, or 21 hours, and the negative effect is jet lag.

As another aspect of the present invention, methods are provided for preventing or reducing one or more adverse effects of jet lag or of a change in a sleep-wake timing cycle in a human subject, wherein the subject alters a usual or Baseline WakeTime and/or a usual or Baseline BedTime by a significant amount, such as by at least 2, 3, 4, 5, 6, 7, 8, 9, 10, 11, 12, 13, 14, 15, 16, 17, 18 or more hours, the method comprising the following steps to or by the subject: administering one or more doses of omega-3 fatty acid, Vitamin C, Vitamin E, Sugar, Caffeine, and/or flavan-3-ols during a travel day and/or 1 to 2 days after, or a day changing sleep and wake times, such as a ChangeDay, and 1 to 2 days after, wherein ChangeDay refers to a day on which the subject commences adjusts the Baseline WakeTime and/or Baseline BedTime to a Destination WakeTime and/or Destination BedTime, such as by at least 2, 3, 4, 5, 6, 7, 8, 9, 10, 11, 12, 13, 14, 15, 16, 17, 18 or more hours; refraining from sleep during the travel or ChangeDay and optionally one or more days after the travel or ChangeDay, except for one or two program naps, wherein the program nap has a selected length and start time; administering a dose of melatonin about 1 hour before a planned sleep time, and optionally administering a dose of melatonin between about 2 hours and about 6 hours before a planned sleep time; after waking from a nap or sleeping a first night after the travel or ChangeDay, administering a dose of Vitamin B12 at actual wake time or within 1 hour after the actual wake time, and optionally administering a dose of Vitamin B12 to the subject between about 2 and about 8 hours after actual wake time; and exposing the subject to or protecting the subject from bright light, green light, blue light, or a combination of these for one or more selected periods.

In some embodiments of the foregoing methods, one or more of caffeine, sugar, and coffee at actual wake time or within 1 hour after the actual wake time. A Program Nap can have a selected length based on a Destination BedTime for the subject, a Baseline WakeTime for the subject, a Date Change for the air travel, if any, and a Time Zone Change for the air travel. A Program Nap can be determined based on Total Wakefulness of the subject during the air travel. The Program Nap can have a selected placement during the air travel based on a Baseline BedTime for the subject, a Destination WakeTime for the subject, a Date Change for the air travel, if any, and a Time Zone Change for the air travel. The Program Nap has a Nap Start Time determined based on a Baseline and/or Usual BedTime and a Nap Remainder. The Program Nap can be adjusted if the placement is within an Unallowed Time Condition and/or if one or more Program Nap Conditions is violated and/or according to one or more Nap Adjustment Rules.

As yet another aspect of the present invention, kits and other products are provided for preventing or reducing one or more adverse effects of air travel in a human subject, comprising: a dose of Vitamin C; a dose of omega-3 fatty acids; optionally a dose of Vitamin E; and instructions for administration of the doses. Kits and other products are also provided for preventing or reducing one or more adverse effects of jet lag, comprising: glasses that substantially block blue and/or green light from the subject; a dose of melatonin; and a dose of Vitamin B12. The foregoing kits can be combined, and/or can further comprise one or more of: a dose of magnesium; a dose of a flavan-3-ol; a dose of glutathione; a dose of vitamin B6; a dose of CoQ10; or a dose of PQQ. In some embodiments, each of the doses is contained in a separate package. In some embodiments, each of the doses may be accessed and consumed without unsealing other doses. In some embodiments, each of the doses is contained in a separate package, in a sachet, in a blister pack or in a dosing glass or plastic bottle.

These and other features and advantages of the present methods and compounds will be apparent from the following detailed description, in conjunction with the appended claims.

DETAILED DESCRIPTION OF THE INVENTION

To facilitate understanding of the present disclosure, various embodiments, terms, and theories are described below. In general, the descriptions herein are for purposes of describing particular embodiments only and are not intended to be limiting. The defined terms are in addition to the technical and scientific meanings of the defined terms as commonly understood and accepted in the technical field of the present teachings.

In one aspect of the present invention, methods and products are provided for preventing or reducing one or more adverse effects of air travel, such as malaise, jet lag, or one or more symptoms of jet lag. Air travel refers to travel by airplane or other vehicle at an altitude. Adverse effects of air travel can include sleeping difficulties, malaise, soreness, stiffness, stomach discomfort, and constipation. When air travel includes a change in time zones, jet lag may be a significant adverse effect of air travel. Jet lag is typically manifested through one or more symptoms of jet lag, such as insomnia or other difficulty falling asleep and/or remaining asleep, difficulty waking at a desired time after the air travel, stomach discomfort, malaise, soreness, stiffness, and others.

In another aspect of the present invention, the methods and products are provided for preventing or reducing one or more adverse effects of a change to a subject's sleep-wake timing cycle, such as a change due to switching between day and night shift work. Adverse effects of a change to a person's sleep-wake timing cycle can include insomnia, difficulty falling asleep and/or remaining asleep, difficulty waking at a desired time, malaise, soreness, stiffness, stomach discomfort, constipation, and others.

The present methods and products can be used to prevent or reduce one or more adverse effects of air travel. As used in this disclosure, adverse effects are prevented or reduced if frequency, duration and/or intensity of one or more such adverse effects is attenuated, diminished, mitigated, cured or eliminated, either temporarily or permanently. Prevention or reduction of adverse effects can be detected using diagnostic techniques or by self-reporting from the subject. The present invention provides a variety of products including compositions, formulations, doses, packages, kits, instructions, and other materials.

In the present disclosure, the term circadian phase refers to a subject's sleep-wake timing cycle. Phase shift refers to moving a subject's sleep-wake timing cycle forward or back. Phase advance refers to moving a subject's sleep-wake timing cycle forward, for traveling east or for going to sleep earlier than usual. Phase delay refers to moving a subject's sleep-wake timing cycle back, for traveling west or for going to sleep later than usual. Jet lag and adverse effects from change to a sleep-wake timing cycle can be prevented or reduced by shifting the subject's circadian rhythm to a destination time zone during or following the air travel and ameliorating adverse effects from an incomplete phase shift and/or a rapid phase shift. The phase-shifting effect is the adjustment of circadian rhythms to align with desired sleep and wake times at the Destination given the Destination time zone.

In some embodiments, air travel comprises trans-meridian travel, which refers to travel across time zones. Air travel may comprise one or more layovers, which refers to time after completing a flight during air travel, but where that air travel did not yet arrive at a Destination and where the traveler is departing on another flight to the Destination. The term inflight refers to time when a traveler is on an airplane. The term "leg" as in "leg of travel" refers to an entire sequence of flights, be it one or more, between a Baseline and Destination. In some embodiments, the present methods and products are suitable for or specially configured for air travel that extends over two, three, four, five, six, seven or more days; and/or for trans-meridian travel across 2, 3, 4, 5, 6, 7, 8, 9, 10, 11, 12, 13, 14, 15, 16, 17, 18, 19, 20, 21, 22 or 23 time zones.

The present methods and products can be used with any subject who travels by air travel and/or has a change to sleep-wake timing cycle, including subjects who are sensitive, average-sensitivity, or insensitive to a reduced amount of sleep. Sensitive refers to a subject who is relatively strongly affected by a reduced amount of sleep (e.g. less than about 6 hours for one night), average-sensitivity refers to a subject who is somewhat affected by a reduced amount of sleep (e.g. less than about 6 hours for one night), while insensitive refers to a person who is largely not affected by a reduced amount of sleep (e.g. less than about 6 hours for one night).

In one aspect of the present invention, methods and products are provided for preventing or reducing one or more adverse effects of air travel. While the present disclosure is not to be bound or limited by theory, it is theorized that air travel produces an inflammatory response in a subject and that the present methods and products prevent or reduce that inflammatory response. It is also theorized that air travel produces diminished mitochondrial function or mitochondrial disfunction and that the present methods and products prevent or reduce that diminished mitochondrial function or mitochondrial disfunction.

In some embodiments, the present methods and products comprise administering one or more agents before, during, and/or after the air travel, such as at selected times before the air travel and/or throughout the air travel. For example, a dose of Vitamin C can be administered between about 1 and about 6 hours (alternatively between about 1.5 and 5 hours) before commencing the air travel. If the subject has multiple flights in one day, the subject should administer multiple doses of Vitamin C, with a dose before each flight. For example, if a first flight commences at 10:00 am and a second flight commences at 3:30 pm, the subject should take 2 doses of Vitamin C that day, at the foregoing selected times before each flight. A selected amount of Vitamin C may be administered in multiple smaller doses of Vitamin C in the period between about 1 and about 5 hours before commencing air travel.

The methods can also comprise administering a dose of omega-3 fatty acids (such as EPA and DHA) between about 1 and about 4 hours before commencing the air travel. The methods may further comprise administering subsequent doses or amounts of Omega-3 fatty acids during the air travel, during one's travel day, and/or for at least one or two days after one's travel day. Doses or amounts can be administered at selected intervals, such as intervals of from about 2 hours to about 4 hours, alternatively at intervals of about 3 hours, during one's travel day. The selected intervals may be influenced by the amount of the doses of Omega-3 fatty acids, in that smaller doses may be administered at shorter intervals, such as at intervals of from about 30 minutes to about 120 minutes, or larger doses may be administered at longer intervals, such as at intervals of from about 4 hours to about 8 hours. By way of example, a method can comprise administering one or more doses of Omega-3 fatty acids at amounts and intervals equivalent to 1,000 mg of Omega-3 fatty acids at 3-hour intervals, such as by administering a dose of 667 mg at intervals of 2 hours. In some embodiments, one or more doses of Omega-3 fatty acids are administered at amounts and intervals equivalent to about 500, about 600, about 750, about 800, about 1000, about 1200, about 1500 or about 2000 mg of Omega-3 fatty acids administered at 3-hour intervals. In some embodiments, one or more doses of Omega-3 fatty acids are administered at amounts and intervals to provide a total daily amount of at least about 1000, about 2000, about 3000, about 4000, about 5000, about 6000 or about 8000 mg of Omega-3 fatty acids.

The methods can also comprise administering a dose of Vitamin E no more than 5 hours before takeoff and no less than 1 hour before flight time. The method can also comprise administering one or more additional doses of Vitamin E at selected intervals, such as intervals of from about 2 hours to about 4 hours, alternatively at intervals of approximately 3 hours during a day of said air travel. The selected intervals may be influenced by the amount of the dose of Vitamin E in that smaller doses may be administered at shorter intervals, such as at intervals of from about 30 minutes to about 120 minutes, or larger doses may be administered at longer intervals, such as at intervals of from about 4 hours to about 8 hours. By way of example, a method can comprise administering one or more doses of Vitamin E at amounts and intervals equivalent to 100 IU of Vitamin E at 3-hour intervals, alternatively equivalent to 50 IU, 150 IU or 200 IU of Vitamin E at 3-hour intervals. In some embodiments, one or more doses of Vitamin E are administered at amounts and intervals to provide a total daily amount of at least about 100 IU, about 300 IU, about 450 IU, about 600 IU, about 750 IU or about 900 IU of Vitamin E. Vitamin E can be co-administered with a dose of Omega-3 fatty acids or administered at different times.

In some embodiments of the present methods and products, the subject is instructed to drink (or otherwise administer) water before the flight (such as about 12 ounces of water in each 2 hour period prior to the flight); to refrain from alcohol during the days of air travel; and/or to brush teeth before any sleep. It is theorized that brushing teeth prevents unnecessary inflammation.

In some embodiments of the present methods and products, a dose of a flavan-3-ol is also administered between about 1 and about 6 hours before commencing air travel (alternatively, between about 1.5 and about 5 hours), including before each leg of air travel. The flavan-3-ol can be co-administered with a dose of Vitamin C or administered at different times. The methods may further comprise administering subsequent doses of a flavan-3-ol at selected intervals, such as at intervals of from about 2 hours to about 4 hours, alternatively at intervals of about 3 hours during one's travel day. The selected intervals may be influenced by the amount of the doses of a flavan-3-ol, in that smaller doses may be administered at shorter intervals, such as at intervals of from about 30 minutes to about 120 minutes, or larger doses may be administered at longer intervals, such as at intervals of from about 4 hours to about 8 hours. By way of example, a method can comprise administering one or more doses of flavan-3-ol at amounts and intervals equivalent to about 500 mg of flavan-3-ol at 3-hour intervals, alternatively equivalent to about 250 mg, about 300 mg or about 600 mg of flavan-3-ol at 3-hour intervals. In some embodiments, one or more doses of flavan-3-ol are administered at amounts and intervals to provide a total daily amount of at least about 500 mg, about 1000 mg, about 1500 mg, or about 2000 mg of flavan-3-ol. The flavan-3-ol doses can be co-administered with a dose of Omega-3 fatty acids or administered at different times. In other embodiments, one or more 15 mg doses of flavan-3-ol are administered at amounts and intervals to provide a total daily amount of about 45 mg, about 90 mg, or about 135 mg of flavan-3-ol.

In some embodiments of the present methods and products, a dose of glutathione and/or a dose of CoQ10 and/or a dose of PQQ, and/or a dose of Vitamin B6 is also administered or provided between about 1 and about 5 hours before commencing air travel, including before each leg of air travel. The doses of these agents can be co-administered with a dose of Vitamin C or administered at different times. The methods may further comprise administering subsequent doses of glutathione, and/or CoQ10, and/or PQQ, and/or a dose of Vitamin B6 at intervals of from about 2 hours to about 4 hours, alternatively at intervals of about 3 hours during one's travel day, starting at waking. The selected intervals may be influenced by the amount of the doses, in that smaller doses may be administered at shorter intervals, such as at intervals of from about 30 minutes to about 120 minutes, or larger doses may be administered at longer intervals, such as at intervals of from about 4 hours to about 8 hours. The doses of these agents can be co-administered with a dose of Omega-3 fatty acids or administered at different times. By way of example, a method can comprise administering one or more doses of CoQ10 at amounts and intervals equivalent to about 50 mg of CoQ10 at 3-hour intervals, alternatively equivalent to about 25 mg, about 100 mg or about 200 mg of CoQ10 at 3-hour intervals. In some embodiments, one or more doses of CoQ10 are administered at amounts and intervals to provide a total daily amount of at least about 50 mg, about 100 mg, about 150 mg, or about 2000 mg of CoQ10. By way of example, a method can comprise administering one or more doses of PQQ at amounts and intervals equivalent to about 10 mg of PQQ at 3-hour intervals, alternatively equivalent to about 5 mg, about 15 mg or about 20 mg of PQQ at 3-hour intervals. In some embodiments, one or more doses of PQQ are administered at amounts and intervals to provide a total daily amount of at least about 10 mg, about 20 mg, about 40 mg, or about 60 mg of PQQ. By way of example, a method can comprise administering one or more doses of Vitamin B6 at amounts and intervals equivalent to about 25 mg of Vitamin B6 at 3-hour intervals, alternatively equivalent to about 10 mg, about 20 mg, about 50 mg or about 100 mg of Vitamin B6 at 3-hour intervals. In some embodiments, one or more doses of Vitamin B6 are administered at amounts and intervals to provide a total daily amount of at least about 20 mg, about 50 mg, about 100 mg, or about 200 mg of Vitamin B6.

In some embodiments of the present methods and products, a dose of ketone salts, ketone esters, and/or medium-chain triglycerides is also administered between about 1 hour before commencing air travel and the commencement of air travel. The methods may further comprise administering subsequent doses of ketone salts, ketone esters, and/or medium-chain triglycerides at intervals of from about 2 hours to about 4 hours, alternatively at intervals of about 3 hours during one's travel day, starting at waking. The selected intervals may be influenced by the amount of the doses, in that smaller doses may be administered at shorter intervals, such as at intervals of from about 30 minutes to about 120 minutes, or larger doses may be administered at longer intervals, such as at intervals of from about 4 hours to about 8 hours. By way of example, a method can comprise administering one or more doses of ketone salts, ketone esters, and/or medium-chain triglycerides at amounts and intervals equivalent to about 20 g at 3-hour intervals, alternatively equivalent to about 10 g, about 30 g, about 50 g or about 75 g at 3-hour intervals. In some embodiments, one or more doses are administered at amounts and intervals to provide a total daily amount of at least about 20 g, about 40 g, about 50 g, or about 100 g. The doses of these agents can be co-administered with a dose of Omega-3 fatty acids or administered at different times.

It is contemplated that the present methods and products are advantageous even when air travel does not include a change in time zone, such as in a flight that is predominantly north to south, south to north, or covering a short distance. However, the present methods and products are also beneficial in preventing or reducing one or more adverse effects wherein the air travel comprises an origin and a destination, and the destination's time zone (referred to as Destination Time Zone or Destination Time) is different from the origin's time zone (referred to as Baseline Time Zone or Baseline Time), such as in east-west or west-east transmeridian travel. The present methods and products are also beneficial for preventing or reducing one or more adverse effects of a change to a subject's sleep-wake timing cycle. In such methods and products, one or more of omega-3 fatty acids, Vitamin B6, CoQ10, PQQ, ketone salts, ketone esters, medium chain triglycerides, and flavan-3-ols can be administered or provided as described above. In such methods and products, Vitamin B12, melatonin, magnesium, sugar, coffee, caffeine can be administered or provided as described below.

In some embodiments, the present methods and products comprise one or more actions, activities or directions to perform or to refrain from, such as sleeping or refraining from sleep. Such actions or activities or directions may be at selected times and/or for selected durations. In some embodiments, the selected times and/or selected durations are determined for the subject based on one or more programs as described herein. Such programs may be based at least in part on Indicated data, which refers to data submitted by the subject, and may provide Program data, such as a method to be followed by the subject or instructions produced by the program.

The term Baseline as used herein refers to any piece of information, condition, parameter or instruction (e.g. bedtime or wake time) corresponding to the subject prior to the air travel. For instance, in a program that provides directions for Chicago to London, Chicago is the Baseline location. In the case of roundtrip travel or a multi-destination trip, each leg of a trip is treated separately as a Baseline-Destination pair. For example, in the case of a roundtrip from Chicago to London, with a layover in New York, on the outbound leg, Chicago is the Baseline location and London is the Destination location. On the return leg of travel, London is the Baseline location and Chicago is the Destination location. In some aspects, Baseline as used herein refers to any piece of information, condition, parameter or instruction (e.g. bed time or wake time) corresponding to the subject prior to a change to sleep-wake timing cycle, regardless of air travel.

The term Destination refers to where the subject ends up after one flight or a series of flights, if there are connecting flights in a given portion of the air travel or a program for the subject's air travel. For example, in the case of a roundtrip from Chicago to London, with a layover in New York, on the outbound leg, Chicago is the Baseline location and London is the Destination location. On the return leg of travel, London is the Baseline location and Chicago is the Destination location. In some aspects, Destination as used herein refers to any piece of information, condition, parameter or instruction (e.g. BedTime or WakeTime) corresponding to the subject after a change to the sleep-wake timing cycle, regardless of air travel.

The term BedTime as used herein refers to the time one indicates or is instructed to go to sleep, such as for Night-Sleep or Nap, and the term WakeTime refers to the time one indicates or is instructed to wake up. NightSleep refers to any sleep period of 6 hours or greater that begins after arrival at a given Destination, starts within 6 hours of Indicated Usual Destination Bedtime and ends within 4 hours of Indicated Usual Destination WakeTime. Nap refers to any rest period that occurs between Program Baseline Waketime and Program Destination NightSleep, and can include sleeping, resting with eyes closed, meditation, and other rest if a subject is unable or does not wish to sleep.

The terms Usual or Routine refer to BedTimes or Wake-Times that a subject regularly follows at Baseline or wishes to regularly follow at Destination. The term FlyDay describes subject provided times surrounding departure and arrival.

a. FlyDay modifies Indicated Baseline WakeTime to refer to a subject-selected WakeTime and Date of that WakeTime before the first flight of a given leg of travel, where the FlyDay Baseline WakeTime can be earlier or equal to Indicated Usual Baseline WakeTime. Indicated Baseline FlyDay WakeTime may be earlier than Indicated Baseline Usual WakeTime on the same calendar day if, for example, travel departs early in the morning, such as at 6 am, to provide the information that the subject must awake earlier than usual to make their flight. If travel departs very early in the morning, such as at 1am, the Indicated Baseline FlyDay WakeTime and Date may occur a day prior to the date of first travel and will indicate this with a date one day before travel.
  i. An example of usage would be a subject who has an Indicated Usual Baseline WakeTime of 7:00 am, but because of a flight leaving on 2/16/19 at 7:30 am, the latest time acceptable to the subject for WakeTime is 5:00 am on 2/16/19 in order to make it to the airport on time, and therefore, the subject provides 05:00 am on 2/16/19 as the Indicated Baseline FlyDay Waketime.
b. FlyDay also modifies Indicated Destination BedTime to refer to a subject selected BedTime and Date of that BedTime after arrival at Destination, where the Indicated Destination FlyDay BedTime can be later than or equal to Indicated Destination Usual BedTime. Indicated Destination FlyDay BedTime may occur on the calendar day of arrival or the calendar day after arrival, if travel arrives late in the evening or the subject chooses to go to sleep after midnight, such as a flight arriving at 11:30 pm where sleep is not possible until 1am the next calendar day.
c. Usual and FlyDay values can be equivalent or different.

When the subject changes time zones (particularly when the subject's Indicated FlyDay Destination BedTime is 2 or more hours later than the subject's Indicated Usual or Routine Baseline BedTime, when those times are transformed into the same time zone (e.g. both in terms of GMT), the present methods and products may comprise administering or providing a dose of Vitamin B12 between about 2 and about 8 hours after waking up, alternately between about 3 and about 6 hours after waking up. In some embodiments, Vitamin B12 is administered between about 2 to about 8 hours after a Program WakeTime, or after an actual wake time if the subject is not employing a method that includes a Program WakeTime. The present methods and products may also comprise exposing the subject to bright light for the period lasting about 1 to about 2 hours starting when taking the dose of Vitamin B12. In some embodiments, to make the dose of Vitamin B12 more effective, the subject is administered or provided the dose of Vitamin B12 at least about 2 hours after the last pre-dose eating and at least about 1 hour before post-dose eating.

In some embodiments, the methods and products also comprise administering a dose of melatonin between about 2 and about 6 hours before a Nap start time or NightSleep start time, alternately between 3 and 6 hours before a Nap start time or NightSleep start time, particularly if the planned nap or NightSleep start time is 1 or more hours before the subject's Indicated Usual Baseline bedtime, when those times are transformed into the same time zone, (e.g. both in terms of GMT). For example, during a trip from Baseline to Destination, Baseline BedTime is 10 pm GMT, and Nap Start Time is 8 pm GMT, so because the Nap Start Time is earlier than Baseline BedTime by 2 hours, the subject would administer a dose of melatonin between 2 and 6 hours before Nap start time, for example at 4 pm GMT. In some embodiments, to make the dose of melatonin more effective, the dose is taken at least about 2 hours after pre-dose eating and at least 1 hour before post-dose eating. The amount in one or more doses or at one or more intervals can be from about 0.1 mg to about 10 mg, alternately from about 0.25 mg to about 5 mg. By way of example, a method can comprise administering one or more doses of melatonin at amounts and intervals equivalent to a single dose of about 1 mg, about 3 mg, about 5 mg, or about 10 mg of melatonin. In some embodiments, one or more doses of melatonin are administered at amounts and intervals to provide a total daily amount of at least about 2 mg, about 3 mg, about 6 mg, about 10 mg, about 12 mg or about 20 mg of melatonin.

In some embodiments of the present methods and products, the methods and products for preventing or reducing adverse effects of air travel, jet lag, and/or change to sleep-wake timing cycle also comprise administering a dose of magnesium between about 2 and about 6 hours before a nap's start time or NightSleep start time, alternately between about 3 and about 6 hours, particularly if the planned nap or NightSleep start time is 1 or more hours before the subject's Indicated Usual Baseline bedtime, when those times are transformed into the same time zone, (e.g. both in terms of GMT). The magnesium can be co-administered with a dose of melatonin or administered at different times.

In some embodiments, the methods comprise refraining from sleep during a portion of said air travel or before or after air travel, except for one or more predetermined sleep periods. In some embodiments, the methods may comprise waking during the travel period after a Program Nap. In some embodiments, the methods may comprise waking after NightSleep.

When a subject wakes from a predetermined sleep period before, during, or after the air travel, a dose of caffeine and/or a dose of coffee and/or a dose of sugar and/or a dose of Vitamin B12 are administered or provided within two hours of waking, preferably within one hour of waking. It is theorized that each of the caffeine, the non-caffeine elements of coffee, sugar, and Vitamin B12 has an independent and valuable effect in preventing or reducing adverse effects of air travel. Caffeinated coffee may sometimes provide both caffeine and coffee, but caffeine and coffee can also be co-administered or administered at different times. In some embodiments, to make the dose of caffeine, dose of coffee, dose of sugar, and/or dose of Vitamin B12 more effective, a meal is eaten about 1 hour after their administration.

In some embodiments, a dose of Vitamin B6 is administered within two hours of waking from a predetermined sleep period during or after the air travel, preferably within one hour of waking. The Vitamin B6 can be co-administered with a dose of caffeine, a dose of coffee, a dose of sugar, and/or a dose of Vitamin B12 or administered at different times.

In some embodiments, from the day on which the subject commences air travel at least through the evening of the day on which the subject arrives at a Destination, the subject is administered doses of omega-3 fatty acids at approximately 3 hour intervals throughout the day, from actual wake time until about 4 hours before sleep time. In some embodiments, the subject continues administering doses omega-3 fatty acids in this manner for at least one or two additional days after arriving at the Destination or Baseline location.

In some embodiments, a dose of melatonin is administered at about one hour before the start of a planned sleep period, such as NightSleep Start Time, or other Program BedTime, especially if that sleep period is longer than about 4.5 hours.

In some embodiments, a dose of magnesium is administered at about one hour before the start of a planned sleep time, such as NightSleep Start Time, or other Program BedTime, especially if that sleep period is longer than about 4.5 hours. The magnesium can be coadministered with a dose of melatonin or administered at different times.

In some embodiments, the subject wears glasses that block bright light and/or blue light and/or green light (or protects the subject's eyes from light in another manner) from 21 to 24 hours after Indicated Baseline Usual or Routine WakeTime. In some embodiments, the subject wears glasses that block bright light and/or blue and/or green light for about 2 hours before going to sleep. If the first time going to sleep after the start of the program is before Indicated Baseline Usual or Routine BedTime, when compared on a constant time zone, wear time increases to about 2.5 hours if going to sleep about 1.5 hours or less before Indicated Usual or Routine Baseline BedTime. The wear time increases to about 3 hours if going to sleep more than about 1.5 hours before Indicated Usual or Routine Baseline bedtime. In some embodiments, the subject wears glasses that block bright light and/or blue light and/or green light (or protects the subject's eyes from light in another manner) from Program Baseline Wake Time, as defined below, until Indicated Usual or Routine Baseline WakeTime, as defined below, if any such difference exists between the two times.

The time of Baseline Program WakeTime and the length of time for NightSleep and Program Nap, as well as the start and end of these periods, is based on various data for the subject, the air travel, and other data. A subject may provide Indicated data and receive Program data for the trip. Inputs will generally take the form of Indicated data, and instructions will generally take the form of Program data; Baseline data or Destination data; Usual or FlyDay data; and BedTime data, WakeTime data, NightSleep data, and start and end times for Nap and NightSleep. The order of these modifiers used in a string does not affect their meaning, and not all descriptions require a selection from each group of modifiers. For example, Program instructions may not require modifiers, such as Usual or FlyDay. Subject may indicate whether they are Sensitive, Average-Sensitivity, or Insensitive to sleep restriction.

In some embodiments, Program Baseline WakeTime, Program NightSleep Start Time, and Program NightSleep End time for a subject is calculated as follows:

1. Set Program Baseline WakeTime to Indicated Baseline FlyDay Wake Time.
2. Set Program NightSleep Start Time to Indicated Destination FlyDay BedTime
3. Set Program NightSleep End Time:
   a. In some embodiments, set Program NightSleep End Time to Indicated Destination Usual WakeTime.
   b. In some embodiments, set Program NightSleep End Time to Indicated Destination Usual WakeTime plus the absolute value of the difference between Indicated FlyDay Destination BedTime and Indicated Usual Destination BedTime, but to no later than a subject provided Latest Possible NightSleep End Time, where this input is provided by a subject.
4. Sleep is not allowed in the following times. If one of these conditions would be breached, move the NightSleep Start Time per the steps below.
   a. Times surrounding flights (Unallowed Time Conditions):
      i. 3 hours before take-off until 0.75 hours after take-off
      ii. 45 minutes before landing until 1.0 hour after landing iii. During a layover
5. In some embodiments, if setting Program NightSleep Start Time to Indicated FlyDay Destination BedTime violates one or more of these conditions, move Program NightSleep Start Time by the minimum amount required to satisfy these conditions, and move Program NightSleep End Time by the same amount.
6. In some embodiments, if setting Program NightSleep Start Time to Indicated FlyDay Destination BedTime violates one or more of these conditions, move Program NightSleep Start Time by the minimum amount required to satisfy these conditions, and change Program NightSleep End Time by the same amount, but to no later than a subject provided Latest Possible NightSleep End Time, where this input is provided by a subject.

In some embodiments, Nap Length for a subject is determined as follows:

1. Time Zone Change is calculated by subtracting the GMT offset for Baseline Time Zone from the GMT offset for Destination Time Zone.
   a. For example, if going from New York (GMT −5 in the winter) to London (GMT −0 in the winter), the Time Zone Change is 0−(−5)=+5.
2. Date Change is calculated by subtracting the calendar date of FlyDay WakeTime in the Baseline Time Zone without regard to the time of day, from the calendar date of Program NightSleep Start Time in the Destination Time Zone without regard to the time of day, to give an integer number of days.
   a. For example, for a trip leaving New York at 9:55 pm EST on 2/15/19, arriving in London at 8:45 am GMT on 2/16/19 with an Indicated Baseline FlyDay Wake-Time of 5:00 am EST on 2/15/19 and a Program NightSleep Start Time of 1:00 am GMT on 2/17/19, the date change is 2/17/19-2/15/19=2.
3. Total Wakefulness is calculated by taking Program NightSleep Start Time, subtracting Indicated Baseline FlyDay WakeTime, Adding [24 times Date Change], and subtracting the Time Zone Change.
   a. For example, for a trip departing from New York City on Feb. 15, 2019, arriving in London on Feb. 16, 2019, if a Program NightSleep Start Time is 11:00 pm (23:00) on 2/16/19, Indicated Baseline FlyDay WakeTime is 7:00 am (07:00) on 2/15/19, the Date Change is +1, and the Time Zone Change is +5, the Total Wakefulness=23−7+1*24−5=35.
4. Nap Length is determined based on the Total Wakefulness and whether a subject indicates they are Sensitive, Average Sensitivity, or Insensitive.
   a. In some embodiments, if the subject is Sensitive, nap length is determined as follows from Total Wakefulness:
      i. 17≤Total Wakefulness, No nap
      ii. 17<Total Wakefulness≤20, Nap Length=20 minutes
      iii. 20<Total Wakefulness≤22.5, Nap Length=1.5 hours iv. 22.5<Total Wakefulness≤26.5, Nap Length=3.0 hours
      v. 26.5<Total Wakefulness≤33, Nap Length=4.5 hours
      vi. 33<Total Wakefulness≤37, Nap Length=6.0 hours
      vii. 37<Total Wakefulness≤46.5, Nap Length=8.0 hours
      viii. 46.5<Total Wakefulness≤49.5, Nap Length=8 hours and 1.5 hours (2 naps)
      ix. 49.5<Total Wakefulness≤55.5, Nap Length=8 hours and 3.0 hours (2 naps)
      x. 55.5<Total Wakefulness, Nap Length=8 hours and 4.5 hours (2 naps)
   b. In some embodiments, if the subject is Average-Sensitivity, nap length is determined as follows from Total Wakefulness:
      i. 18≤Total Wakefulness, No nap
      ii. 18<Total Wakefulness≤21.5, Nap Length=20 minutes
      iii. 21.5<Total Wakefulness≤24, Nap Length=1.5 hours iv. 24<Total Wakefulness≤28, Nap Length=3.0 hours
      v. 28<Total Wakefulness≤36, Nap Length=4.5 hours vi.
      36<Total Wakefulness≤42, Nap Length=6.0 hours
      vii. 42<Total Wakefulness≤48.8, Nap Length=8.0 hours
      viii. 48.5<Total Wakefulness≤51, Nap Length=8 hours and 1.5 hours (2 naps)
      ix. 51<Total Wakefulness≤57, Nap Length=8 hours and 3.0 hours (2 naps)
      x. 57<Total Wakefulness, Nap Length=8 hours and 4.5 hours (2 naps)
   c. In some embodiments, if the subject is Insensitive, nap length is determined as follows from Total Wakefulness:
      i. 19.5≤Total Wakefulness, No nap
      ii. 19.5<Total Wakefulness≤23, Nap Length=20 minutes
      iii. 23<Total Wakefulness≤25.5, Nap Length=1.5 hours
      iv. 25.5<Total Wakefulness≤29.5, Nap Length=3.0 hours
      v. 29.5<Total Wakefulness≤37.5, Nap Length=4.5 hours vi.
      37.5<Total Wakefulness≤43.5, Nap Length=6.0 hours vii. 43.5<Total Wakefulness≤49.5, Nap Length=8.0 hours
      viii. 49.5<Total Wakefulness≤52.5, Nap Length=8 hours and 1.5 hours (2 naps)
      ix. 52.5<Total Wakefulness≤58.5, Nap Length=8 hours and 3.0 hours (2 naps)
      x. 58.5<Total Wakefulness, Nap Length=8 hours and 4.5 hours (2 naps)
      In some embodiments, the foregoing values for Total Wakefulness are +/−15%, alternatively +/−10%, alternatively +/−5%.

In some embodiments, Nap Placement for a subject is determined as follows:
   1. The Nap Interval is calculated by taking the Indicated Destination Usual WakeTime, subtracting the Indicated Baseline Usual BedTime, subtracting the Time Zone Change, and adding [24 times Date Change].
      a. For example on a trip from New York City departing 2/15/19 to London arriving 2/16/19, if a client's Indicated Destination Usual Waketime is 7 am (07:00), Indicated Baseline usual BedTime is 11 pm (23:00), and Time Zone Change is +5, the Nap Interval is: [07:00]−[23:00]−[5]+[1*24]=3 hours
   2. The Nap Remainder is calculated by subtracting the Nap Length from the Nap Interval.
      a. For example on a trip from New York City departing 2/15/19 to London arriving 2/16/19, if a client's Indicated Destination Usual Waketime is 7 am (07:00), Indicated Baseline usual BedTime is 11 pm (23:00), and Time Zone Change is +5, the Nap Interval is: [07:00]−[23:00]−[5]+[1*24]=3 hours. With a Nap Length of 4.5 hours, the Nap Remainder is: 3−4.5=−1.5. This can be a positive or negative value.
   3. To calculate the Nap Start Time, do the following. If the Nap Length calculation provides 2 naps, follow this procedure with the longer nap.
      a. In some embodiments, take the Indicated Baseline Usual BedTime, add the Nap Remainder divided by between 1.5 and about 2.5, alternately divided by 2, and that is the Nap Start Time. Check if this timing is allowed per the conditions below.
         i. For example, if Indicated Baseline BedTime is 23:00 EST and the Nap Remainder is −1.5, the Nap should start at 23+(−1.5)/2=22:15 EST.
      b. In some embodiments, take the Indicated Baseline Usual BedTime, add the Nap Remainder divided by between 1.5 and about 2.5, alternately divided by 2, subtract the absolute value of the difference between Indicated Baseline Usual WakeTime and Indicated FlyDay Baseline WakeTime, and add the absolute value of the difference between Program NightSleep Start Time and Indicated Usual Destination BedTime.

i. For example, if Indicated Baseline Usual BedTime is 23:00 EST and the Nap Remainder is −1.5, Indicated Baseline Usual WakeTime is 07:00, Indicated FlyDay Baseline WakeTime is 6:00, Program NightSleep Start Time is 22:00, and Indicated Usual Destination BedTime is 22:00, the Nap should start at [23]+[1.5/2]−[7−6]+[22−22]=21:15 EST 4. Sleep is not allowed during the following times. If one of these conditions is breached, move the Nap Start Time per the below.
   c. Times surrounding flights (Unallowed Time Conditions):
      i. 3 hours before take off until 0.75 hours after take-off
      ii. 0.75 hours before landing until 1.0 hour after landing
      iii. During a layover
   d. Proximity to Program Baseline WakeTime or Program NightSleep (Program Nap Conditions)
      i. Sleep should not violate the following rules
      ii. A Nap Length of 1.5 hours should end at least 6 hours before Program NightSleep Start Time and should start at least 4 hours after Program Baseline WakeTime
      iii. A Nap Length of 3 hours should end at least 8 hours before Program NightSleep Start Time and should start at least 6 hours after Program Baseline WakeTime iv. A Nap Length of 4.5 hours should end at least 10 hours before Program NightSleep Start Time and should start at least 8 hours after Program Baseline WakeTime
      v. A Nap Length of 6 hours should end at least 12 hours before Program NightSleep Start Time and should start at least 10 hours after Program Baseline WakeTime vi. A Nap Length of 8 hours should end at least 14 hours before Program NightSleep Start Time and should start at least 12 hours after Program Baseline WakeTime
   e. Maximum Time Awake
      i. A Sensitive subject should not have a time period of more than about 20 hours without sleep. An Average-Sensitivity subject should not have a time period of more than about 21 hours without sleep. An Insensitive subject should not have a time period of more than about 22 hours without sleep.

5. Rules for modifying Nap Start Time and/or Nap Length (Nap Adjustment Rules). It is contemplated that one or more tentative Nap Start Times and/or tentative Nap Lengths may be calculated, and then recalculated or iteratively adjusted to provide a final Nap Start Time and/or a final Nap Length.
   a. When Total Wakefulness calls for 1 nap: If Nap Start Time causes a violation of sleep restrictions (as described above), move Nap Start Time the minimum amount such that it does not violate any conditions. If no alternate timing satisfies all conditions, move Program NightSleep Start Time up to 1.5 hours and reattempt to move the Nap Start Time to find an acceptable value with the minimum of change. If this does not satisfy conditions, reduce Nap Length by 1.5 hours and restart the Nap Start Time Calculation, iteratively if required.
   b. If Total Wakefulness calls for 2 naps and the longer nap violates these conditions, attempt the shorter nap. If this does not satisfy conditions, return to the longer nap
      and move the Start Time the minimum amount required such that it does not violate any conditions. If no alternate timing satisfies all conditions, return to the shorter nap and move the Start Time the minimum amount required such that it does not violate any conditions. If no acceptable conditions are found, move the NightSleep Start Time by up to 1.5 hours, then try placing the longer nap and if unsuccessful, then the shorter nap, each moving the minimum amount to satisfy all conditions. If both naps still fail one or more conditions, reduce the longer nap from 8 to 6 hours and restart the Nap Start Time Calculation with this longer nap. If this still violates the conditions, reduce it further by 1.5 hours and restart the Nap Start Time Calculation, iteratively if required, until an acceptable Nap Start Time and Nap Length combination are found for the longer nap.

6. Rules for Identifying and Modifying Nap 2 Start Time and/or Nap 2 Length (Nap Adjustment Rules)
   a. Nap 2 Start Time Calculation. After placing the first nap in a program with two naps, place the second nap by calculating the Second Nap Interval. This is calculated by finding the midpoint of the interval between the Program NightSleep Start Time, as modified, and the first Nap End Time to give the Nap 2 Interval Midpoint. The middle of the second Nap is set at the Nap 2 Interval Midpoint, giving a corresponding Nap 2 Start Time of the Nap 2 Interval Midpoint minus half the Nap 2 Length.
   c. Rules for modifying Nap Start Time and/or Nap Length. If starting Nap 2 at Nap 2 Start Time causes a violation of the sleep restrictions described above for a single nap, move Nap 2 Start Time the minimum amount such that it does not violate any conditions. If it is not possible to satisfy the conditions, reduce Nap Length by 1.5 hours and restart the Nap 2 Start Time Calculation, iteratively reducing the length if required.

The terms "administering" and "administration" are used to describe taking, ingesting or otherwise receiving a dose. A dose may be administered in various ways including oral (e.g., ingestion), intragastric, and parenteral (referring to intravenous and intra-arterial and other appropriate parenteral routes), among others. Administration can be continuous or at distinct intervals. A dose can be administered or provided as one dosage form or in multiple dosage forms. A dose can be in a dosage form, such as a solid oral dosage form or a liquid oral dosage form. Suitable dosage forms include tablets, capsules, sachets, beverages, etc.

In the present methods and products, one or more agents may be administered or provided to a subject. The terms "coadminister" and "coadministration" are used to describe administration of at least one of the foregoing agents in combination with at least one other agent. For example, magnesium can be coadministered with melatonin. As another example, a flavan-3-ol and/or a glutathione can be coadministered with Vitamin C. When two or more agents are coadministered, they are administered at approximately the same time. Two or more agents for coadministration are provided in a single dosage form or in separate dosage forms. The term combination therapy is used to describe the administration of at least one of the foregoing agents in combination with at least one other agent, either through coadministration of the agents, or through administration at different times. Alternatively, the agent selected for combination therapy may be administered at different times to the patient. Of course, the present compounds may be combined with other agents as required.

Vitamin C is administered or provided in some embodiments of the present methods and products. Vitamin C is also referred to as ascorbic acid or L-ascorbic acid.

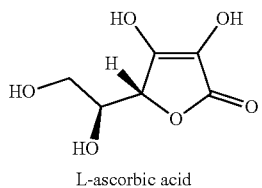 [SMILES: O=C1O[C@H]([C@@H](O)CO)C(O)=C1O]

L-ascorbic acid

As used herein, the term Vitamin C also encompasses salts of ascorbic acid (such as sodium ascorbate and calcium ascorbate) and the oxidized form of ascorbic acid (dehydroascorbic acid), as well as derivatives of ascorbic acid. Examples of derivatives of Vitamin C are described in Sloan U.S. Pat. No. 9,550,744. The amount in one or more doses or at one or more intervals can be from about 50 to about 2000 mg, alternatively from about 250 to about 1250 mg.

A flavan-3-ol (or flavanol) is administered or provided in some embodiments of the present methods and products. Flavan-3-ols are derivatives of flavan and are found in a wide array of phytochemical-bearing foods, such as blueberries, raspberries, red wine, chocolate, and teas. The flavan-3-ol can be a single component, a mixture of components, or a whole extract from a fruit or other plant. Flavan-3-ols include catechin, epicatechin, epigallocatechin, epigallocatechin gallate, proanthocyanidins, theaflavins, and thearubigins. The amount in one or more doses or at one or more intervals can be from about 5 to about 1,000 mg, alternatively from about 10 to about 750 mg.

Glutathione is administered or provided in some embodiments of the present methods and products. Glutathione is also referred to as GSH or (2S)-2-Amino-4-{[(1R)-1[(carboxymethyl)carbamoyl]-2-sulfanylethyl]carbamoyl}butanoic acid.

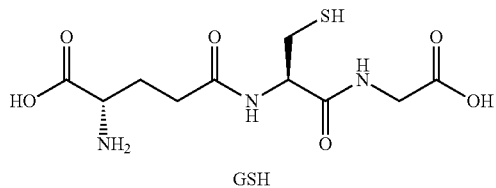 [SMILES: N[C@@H](CCC(=O)N[C@@H](CS)C(=O)NCC(=O)O)C(=O)O]

GSH

As used herein, the term glutathione also encompasses salts thereof. Glutathione will generally be employed in its reduced (GSH), though in some embodiments it may be employed in its oxidized (GSSG) form. Glutathione also encompasses derivatives of GSH. Examples of derivatives of GSH include esters of GSH, and are described in Sakon et al. U.S. Pat. No. 6,627,732. The amount in one or more doses or at one or more intervals can be from about 50 to about 1,000 mg, alternatively from about 100 to about 750 mg.

Omega-3 fatty acid(s) is administered or provided in some embodiments of the present methods and products. Omega-3 fatty acids are polyunsaturated fatty acids having a double bond three atoms away from the terminal methyl group. Preferred omega-3 polyunsaturated fatty acids include eicosapentaenoic acid (EPA), docosahexaenoic acid (DHA), eicosatetraenoic acid (ETA) and docosapentaenoic acid (DPA), 18-hydroxy-eicosapentaenoic acid (18-HEPE), 17-hydroxy-docosahecaneoic acid (17-HDHA), and 14-hydroxydocosahexaenoic acid (14-HDHA), especially mixtures of EPA and DHA.

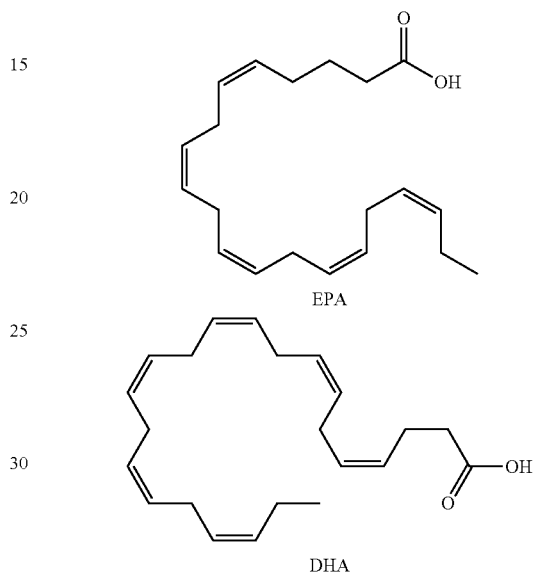

Omega-3 fatty acids generally include any food-grade lipid or mixture of lipids comprising free omega-3 polyunsaturated fatty acid or fatty-acid derivative (including tri-, di-, and monoglycerides and phospholipids). As used herein, fatty acids include the corresponding fatty acid residues in derivatives thereof that provide the fatty acid when digested, such as triglycerides, diglycerides, monoglycerides and phospholipids of said fatty acids. The amount in one or more doses or at one or more intervals can be from about 10 to about 5,000 mg, alternatively from about 250 to about 2,000 mg.

A ketone salt and/or ketone ester is administered or provided in some embodiments of the present methods and products. Ketone salts or esters include acetoacetate, 1,3-butanediol acetoacetate monoester, 1,3-butanediol acetoacetate diester, or R,S-1,3-butanediol-diacetoacetate ester. Preferred examples of ketone supplements include the ketone esters R,S-1,3-butanediol acetoacetate monoester (BD-AcAc); R,S-1,3-butanediol acetoacetate diester (BD-AcAc$_2$); (R)-3hydroxybutyl(R)-3-hydroxybutyrate; R-beta-hydroxybutyrate, acetoacetate, and mixtures thereof.

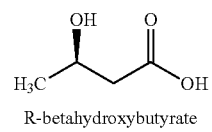

R-betahydroxybutyrate

The amount in one or more doses or at one or more intervals can be from about 3 to about 50 g, alternatively from about 10 to about 30 g.

A branched or unbranched medium chain-triglyceride or combination of medium-chained triglycerides is administered or provided in some embodiments of the present methods and products. Branched or unbranched Medium chain triglycerides include triglycerides containing between 6 and 10 carbon atoms. Medium chain triglycerides include caproic acid, caprylic acid, capric acid, 2-propyloctanoic acid, and lauric acid. Preferred examples of medium chain triglyceride supplements include caprylic acid and capric acid. The amount in one or more doses or at one or more intervals can be from about 3 to about 50 g, alternatively from about 7 to about 25 g.

Vitamin E is administered or provided in some embodiments of the present methods and products. The amount in one or more doses or at one or more intervals can be from about 2 to about 450 IU, alternately from about 5 to about 200 IU. Vitamin E is the general name for a class of eight compounds: four isomers of tocopherol (alpha-tocopherol, beta-tocopherol, gamma-tocopherol, delta-tocopherol) and four isomers of tocotrienol (alpha-tocotrienol, betatocotrienol, gamma-tocotrienol, delta-tocotrienol).

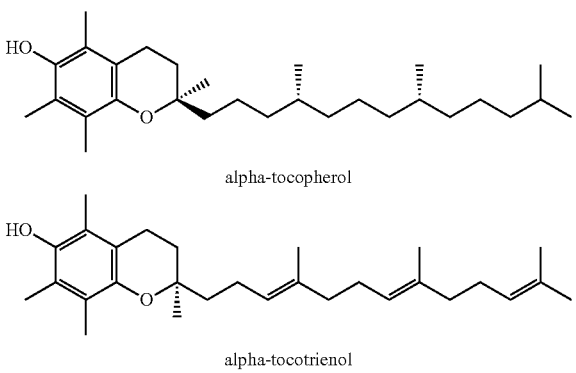

alpha-tocopherol alpha-tocotrienol

Tocopherols and tocotrienols are sometimes collectively called tocols. The amount in one or more doses or at one or more intervals can be from about 1.0 to about 200 mg, alternatively from about 3 to about 50 mg.

Vitamin B12 is administered or provided in some embodiments of the present methods and products. Vitamin B12 is also called also called cobalamin, though it can be provided in its methylcobalamin or cyanocobalamin forms. The amount in one or more doses or at one or more intervals can be from about 5 to about 5000 µg, alternatively from about 50 to about 1500 µg.

Vitamin B6 is administered or provided in some embodiments of the present methods and products. Vitamin B6 refers to a group of chemically similar compounds which interconvert in vitro, such as pyridoxal phosphate:

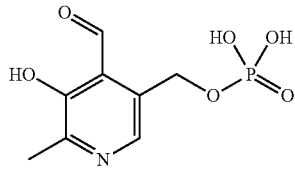 [SMILES: Cc1ncc(COP(=O)(O)O)c(C=O)c1O]

Vitamin B6 encompasses pyridoxines, pyridoxals and pyridoxamines, and esters and salts thereof. Vitamin B6 derivatives are described in Goerne U.S. Publication No. 20090054371 and Weber et al. U.S. Publication No. 20140308691. The amount of Vitamin B6 in one or more doses or at one or more intervals can be from about 0.1 to about 100 mg, alternatively from about 1 to about 50 mg.

Co-enzyme Q10 (CoQ10) is administered or provided in some embodiments of the present methods and products. Co-enzyme Q10 is also referred to as 2,3-dimethoxy-5-methyl-6decaprenil-1,4-benzoquinone or ubiquinone.

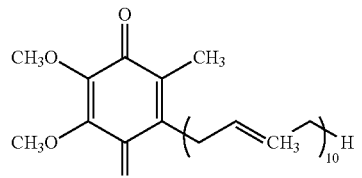

2,3-dimethoxy-5-methyl-6-decaprenil-1,4-benzoquinone

As used herein, the term CoQ10 also encompasses salts and derivatives of Co-enzyme Q10. The amount of CoQ10 in one or more doses or at one or more intervals can be from about 10 to 500 mg, alternately from 50 to 250 mg.

Pyrroloquinoline quinone (PQQ) is administered or provided in some embodiments of the present methods and products. PQQ is also referred to as methoxatin.

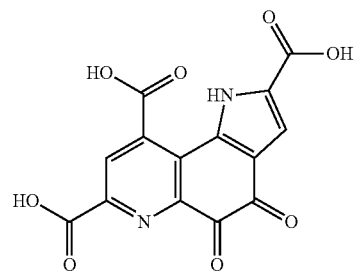

pyrroloquinoline quinone

As used herein, the term PQQ encompasses salts, esters and derivatives of pyrroloquinoline quinone. Examples of derivatives of PQQ are described in Ikemoto et al. U.S. Publication No. 20150037308. The amount in one or more doses or at one or more intervals can be from about 1 to about 40 mg, alternatively from about 5 to about 20 mg.

Melatonin is administered or provided in some embodiments of the present methods and products. Melatonin is also known as N-acetyl-5-methoxytryptamine.

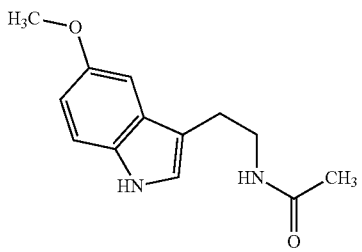

N-acetyl-5-methoxytryptamine

As used herein, the term melatonin also encompasses salts and derivatives thereof. Examples of derivatives of N-acetyl-5-methoxytryptamine are described in Ducrocq et al. U.S. Pat. No. 6,436,984 and Escames Rosa et al. U.S. Publication No. 20150306072. The amount in one or more doses or at one or more intervals can be from about 0.1 mg to about 10 mg, alternately from about 0.25 mg to about 5 mg.

Magnesium is administered or provided in some embodiments of the present methods and products. As used herein, the term Magnesium encompasses salts, amino-acid chelates, and other chemical forms of Magnesium. The amount in one or more doses or at one or more intervals can be from about 10 to about 500 mg, alternately from about 25 to about 250 mg.

Caffeine is administered or provided in some embodiments of the present methods and products. As used herein, the term caffeine encompasses salts and derivatives of caffeine. The amount in one or more doses or at one or more intervals can be from about 10 to about 400 mg, alternately from about 50 to about 300 mg. Caffeine can be administered by drinking coffee or consuming another caffeinated beverage or food. Coffee and over beverages can vary in their amount of caffeine, though a typical amount is 95 mg in 8 ounces of coffee. In some embodiments, the dose of caffeine can be at least about 50 mg, about 75 mg, about 90 mg, about 100 mg, about 125 mg, about 150 mg, or more. In some embodiments the dose of caffeine can be a maximum of about 500 mg, about 450 mg, about 400 mg, about 350 mg, about 300 mg, or about 250 mg. The foregoing maximums and minimums can be combined to form a range.

Sugar is administered or provided in some embodiments of the present methods and products. As used herein, the term sugar encompasses sucrose and other natural and artificial sweeteners, particularly those that provide calories or food energy to a subject. The amount of sugar in one or more doses or at one or more intervals can be from about 5 g to about 75 g, alternately from about 7.5 grams to about 30 grams.

It is contemplated that the foregoing agents may be provided as nutritionally or pharmaceutically acceptable salts, esters, derivatives, or in other forms.

As mentioned above, an amount of an agent can be provided in a single dose or divided between multiple doses over a longer time period. In some embodiments, an amount of 1000 mg to be administered at a selected timepoint may be administered in two doses of 500 mg at times before and after the selected timepoint.

In some embodiments, a subject is exposed to or protected from light, such as bright light, blue light, and/or green light. Bright light encompasses light having an intensity of about 500 lux to about 120,000 lux. Blue light encompasses light having a wavelength of about 380 nm to about 500 nm. Green light encompasses light having a wavelength of about 500 to about 565 nm. For instance, a subject may be exposed to bright light throughout the period from WakeTime until NightSleep, except when protected from bright light, blue light, and/or green light, and/or a subject may be protected from bright light, blue light, and green light for a period of about 2 hours before planned sleep time. A subject can be protected from bright light, blue light, and/or green light by wearing glasses tinted to substantially block all light, blue light, and/or green light, such as amber-tinted glasses, orange-tinted glasses, or red-tinted glasses. When sleeping, it is assumed a subject is protected from light. A subject can be exposed to bright light, blue light, and/or green light by removing glasses tinted to substantially block one or more colors of light, spending time outside, raising window shades, or activating bright light sources.

In some embodiments, a subject eats a low-carbohydrate meal or snack at a planned time. The term meal generally refers to a subject's main intake of food or sustenance in a day, such as breakfast, lunch or dinner, while a snack is a relatively smaller intake, typically between meals. In some cases, a meal and a snack can be distinguished by size, with a meal comprising about at least 350 calories, alternatively at least about 450 calories, and a snack is less than 350 calories, alternatively about 300 calories or less. In some embodiments, a subject eats a meal or snack at a planned time, where the planned time generally refers to the time at which the subject does most of eating. For instance, when a subject eats a meal at a time between about one and about five hours before commencing air travel, it is contemplated that the subject begins eating within that period. A low-carbohydrate meal or snack typically has less than about 30% of its calories derived from carbohydrate.

As another aspect of the present invention, the methods and products described herein can be adapted for preventing or reducing one or more adverse effects of a change to a subject's sleep-wake timing cycle without trans-meridian travel. In the context of this aspect, the descriptions related to "Destination", such as Destination WakeTime and Destination BedTime, can be adapted as "Changed", such as Changed WakeTime and Changed BedTime. A Changed WakeTime and Changed BedTime can be selected to reflect the subject's changed work shift or lifestyle. Descriptions related to air travel such as FlyDay can be adapted to ChangeDay. The foregoing methods of calculating Nap Start Time, Nap Length, NightSleep parameters, and others can be adapted by providing the desired Indicated Changed Usual Destination WakeTime and SleepTime and the Indicated Changed ChangeDay WakeTime and SleepTime, with the Time Zone Change set to 0.

EXAMPLES

Example 1

Subjects are provided doses of agents and instructions to practice a method of preventing or reducing adverse effects of air travel. The agents were administered as follows:

TABLE 1

| Agent | Amount | Selected Times |
|---|---|---|
| Ascorbic acid (Vitamin C) | 1,000 mg per dose | one to five hours before air travel |
| omega-3 fatty acids | 1,000 mg per dose | one to three hours before air travel, and 3-hour intervals during the day of air travel |
| Mixed Tocopherols (Vitamin E) | 7.5 mg per dose | one to three hours before air travel, and 3-hour intervals during the day of air travel |
| Methyl-cobalamin (Vitamin B12) | 1,000 mcg per dose | 3 to 8 hours after actual wake time if Nap Start Time (or NightSleep Start Time, whichever occurs first) is 2 or more hours after Indicated Baseline SleepTime |
| Melatonin | 0.9 mg, 1.8 mg, or 2.7 mg per dose | 3 to 6 hours before going to sleep if Nap Start Time (or NightSleep Start Time, whichever occurs first) is one or more hours before Indicated Baseline SleepTime |
| Sugar | 16 g or 22 g per dose | within two hours of waking from Program Nap, if the Nap Wake Time is within 5 hours of Indicated Destination BedTime, and within one hour after waking from the first program NightSleep |

TABLE 1-continued

| Agent | Amount | Selected Times |
|---|---|---|
| Coffee, including the caffeine naturally occurring in it | 16 oz or 20 oz of coffee, containing 160 mg or 200 mg, per dose | within two hours of waking from Program Nap, if the Nap Wake Time is within 5 hours of Indicated Destination BedTime, and within one hour after waking from the first program NightSleep |
| Methyl-cobalamin (second instruction) | 1,000 mcg per dose | within two hours of waking from Program Nap, if the Nap Wake Time is within 5 hours of Indicated Destination BedTime, and within one hour after waking from the first program NightSleep |
| Melatonin (second instruction) | 0.9 mg, 1.8 mg, or 2.7 mg per dose | within one hour before Program BedTime |

The subjects were also instructed to refrain from sleep during the air travel except for one or two program naps, wherein the program nap(s) has a selected length and start time. The subjects were also instructed to aim to drink 12 oz. of water every 2 hours prior to the flight; avoid alcohol during program days; and brush teeth before any sleep.

Example 2

In this example, subjects practiced various embodiments of the method of Example 1, with some variations in particular times of administering doses. The number of subjects and nature of their air travel is set forth in Table 2.

TABLE 2

| Number of 1-Way Trips with Time Zone Changes | 123 |
|---|---|
| 1-Way trips with 4+ hour time change | 74 |
| 1-Way trips with 1-3 hour time change | 49 |
| Number of Distinct Travelers | 34 |

The subjects were subsequently surveyed as to the effect of the doses and instructions, in terms of how they felt relative to a trip without the doses and instructions. Table 3 sets forth the survey results.

TABLE 3

| Feeling relative to a trip without the present method | Much Better | Modestly Better | No benefit | No feedback provided |
|---|---|---|---|---|
| 1 Way Trips with 4+ Hour Time Change | 57 | 3 | 1 | 13 |
| 1 Way Trips with 1-3 Hour Time Change | 46 | 0 | 3 | 0 |

The survey results indicate that a high majority of the subjects felt much better after practicing the method, compared to air travel without the method. Approximately 94% of subjects traveling by air to a destination with a 1-3 hour time change reported that they felt much better. Approximately 93% of subjects reporting the effect after traveling by air to a destination with a time change of 4 hours or more reported that they felt much better.

Example 3

In this example, a subject practices a method of preventing or reducing adverse effects of air travel and jet lag.

TABLE 2

| TIME | ACTIVITY |
|---|---|
| \multicolumn{2}{c}{Day 1} | |
| 06:30 PDT | Eat a lower-carbohydrate meal. |
| 09:30 PDT | Eat a lower-carbohydrate snack, and take 1 omega-3. |
| 12:30 PDT | Eat a lower-carbohydrate meal, and take 1 omega-3. |
| 14:30 PDT | Take 1 Melatonin capsule. |
| 15:30 PDT | Eat a lower-carbohydrate snack, and take 1 omega-3 softgel and 1 vitamin C capsule. |
| 17:15 PDT | Depart LAX. |
| 17:30 PDT | Start avoiding light, but don't sleep. Wear the blue- and green-light blocking glasses provided. To further minimize light exposure, turn off overhead lights, and use software on any computer to minimize blue light output. |
| 19:30 PDT | Take 1 Melatonin capsule and 1 omega-3 softgel. |
| 20:30 PDT/ 05:30 BST | Sleep for 3.0 hours. |
| \multicolumn{2}{c}{Day 2} | |
| 08:30 BST | Wake up. Take 1 vitamin B-12, and drink a large cup of sugar-sweetened coffee. A sweetened coffee packet is provided, which you can mix with 18 oz. of hot or cold water. Expose yourself to as much bright light as possible for the next hour. |
| 09:30 BST | Eat a lower-carbohydrate meal, and take 1 omega-3. |
| 11:45 BST | Arrive LHR. |
| 12:30 BST | Start avoiding light as much as possible and put on the orange glasses until 15:30 BST. Eat a lower-carbohydrate snack, and take 1 omega-3. |
| 15:30 BST | Remove the glasses, and maximize your light exposure. Eat a lower-carbohydrate meal. |
| 18:30 BST | Eat a lower-carbohydrate snack. |
| 21:00 BST | Start avoiding light as much as possible for the rest of the night, including using the blue- and green-light blocking glasses. |
| 22:00 BST | Take 1 melatonin capsule. |
| 23:00 BST | Sleep for 7 hours. |

TABLE 2-continued

| TIME | ACTIVITY |
|---|---|
| | Day 3 |
| 05:00 BST | Wake up. Take 1 vitamin B-12, and drink a large cup of coffee with 3 packets of sugar. Expose yourself to as much bright light as possible throughout the day. |
| 06:00 to 19:00 BST | Eat lower-carbohydrate meals or snacks at 06:00 and every ~3 hours after until dinner around 19:00. Take 1 omega-3 pill with each meal/snack. |
| 21:00 BST | Reduce light exposure for the rest of the night. Turn off whatever lights you can, and use the blue- and green-light blocking glasses. |
| 22:00 BST | Take 1 melatonin capsule. |
| 23:00 BST | Sleep. |

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present teachings, some exemplary methods and materials are now described.

As used herein, the terms "substantial" or "substantially" mean to within acceptable limits or degree to one having ordinary skill in the art. For example, "substantially free" of an item means that one skilled in the art considers the amount of the item to be insignificant or without effect. The terms "approximately" and "about" mean to within an acceptable limit or amount to one having ordinary skill in the art. The term "about" generally refers to plus or minus 15% of the stated number. For example, "about 10" may indicate a range of 8.5 to 11.5. As another example, "approximately the same" means that one of ordinary skill in the art considers the items being compared to be the same. It is intended that, whenever this disclosure provides a numerical value preceded by approximately or about, the exact number is also disclosed. For instance, a disclosure of at least about 2 hours also discloses at least 2 hours. In the present disclosure, numeric ranges are inclusive of the numbers defining the range.

As used in the specification and appended claims, the terms "a," "an," and "the" include both singular and plural referents, unless the context clearly dictates otherwise. Thus, for example, "an agent" includes one agent and plural agents.

All patents and publications referred to herein are expressly incorporated by reference.

EXEMPLARY EMBODIMENTS

Exemplary embodiments provided in accordance with the disclosed subject matter include, but are not limited to, the following:

[1] A method for preventing or reducing one or more adverse effects of air travel in a subject in need thereof, wherein the method comprises administering to the subject simultaneously, at different times or at selected intervals one or more antioxidant agents, and/or one or more anti-inflammatory agents, and/or one or more mitochondrial support agents.

[2] The method according to embodiment 1, wherein the one or more antioxidant agents comprise vitamin C, vitamin E, glutathione, flavan-3-ols, and any combinations thereof.

[3] The method according to any of the preceding embodiments, wherein the one or more anti-inflammatory agents comprise omega-3 fatty acids, flavan-3-ols, magnesium, and any combinations thereof.

[4] The method according to any of the preceding embodiments, wherein the one or more mitochondrial support agents comprise ketone salts or esters, medium chain triglycerides, Co-Enzyme Q10, pyrroloquinoline quinone, vitamin B6, and any combinations thereof.

[5] The method according to any of the preceding embodiments, wherein the one or more adverse effects of air travel comprise one or more of sleeping difficulties, malaise, soreness, stiffness, stomach discomfort, and constipation; and wherein the method comprises administering to the subject an antioxidant agent and an anti-inflammatory agent, or an antioxidant agent and a mitochondrial support agent, or an antioxidant agent, an anti-inflammatory agent, and a mitochondrial support agent.

[6] The method according to any of the preceding embodiments, wherein the method comprises administering to the subject a dose of the antioxidant agent between about one and about five hours before commencing air travel; and administering to the subject a dose of the anti-inflammatory agent between about one and about five hours before commencing said air travel. [7] The method according to any of the preceding embodiments, wherein the method further comprises administering to the subject one or more additional doses of anti-inflammatory agent during air travel day.

[8] The method according to any of the preceding embodiments, wherein the method further comprises administering to the subject one or more additional doses of antioxidant during air travel day.

[9] The method according to any of the preceding embodiments, wherein the anti-inflammatory agent is omega-3 fatty acids, and the antioxidant agent is vitamin C and/or vitamin E.

[10] The method according to any of the preceding embodiments, wherein the subject changes time zones by at least 2, 3, 4, 5, 6, 7, 8, 9, 10, 11, 12, 13, 14, 15, 16, 17, 18, 19, 20, or 21 hours as a result of air travel.

[11] The method according to any of the preceding embodiments, wherein the one or more adverse effects of air travel further comprise jet lag.

[12] The method according to any of the preceding embodiments, wherein the method comprises administering to the subject a dose of omega-3 fatty acids between about 1 and 4 hours before commencing the air travel.

[13] The method according to any of the preceding embodiments, wherein the method further comprises administering to the subject one or more additional doses of omega-3 fatty acids during air travel day.

[14] The method according to any of the preceding embodiments, wherein the method further comprises administering to the subject a dose of vitamin C and/or vitamin E between about 1 and about 5 hours before commencing air travel.

[15] The method according to any of the preceding embodiments, wherein the method further comprises administering to the subject one or more additional doses of omega-3 fatty acids, vitamin C, and/or vitamin E during air travel day.

[16] A method for preventing or reducing one or more adverse effects of jet lag or one or more adverse effects of a change in sleep-wake timing cycle in a subject in need thereof, wherein the method comprises administering to the subject simultaneously, at different times, or at selected intervals, one or more antioxidant agents, and/or one or more anti-inflammatory agents, and/or one or more mitochondrial support agents, and/or one or more circadian shift support agents.

[17] The method according to embodiment 16, wherein the one or more antioxidant agents comprise vitamin C, vitamin E, glutathione, flavan-3-ols, and any combinations thereof.

[18] The method according to any of preceding embodiments 16 and 17, wherein the one or more anti-inflammatory agents comprise omega-3 fatty acids, flavan-3-ols, magnesium, and any combinations thereof.

[19] The method according to any of preceding embodiments 16-18, wherein the one or more mitochondrial support agents comprise ketone salts or esters, medium chain triglycerides, Co-Enzyme Q10, pyrroloquinoline quinone, vitamin B6, and any combinations thereof.

[20] The method according to any of preceding embodiments 16-19, wherein the one or more one or more circadian shift support agents comprise vitamin B12, vitamin B12 and exposure or intentional increase of exposure to light, melatonin, caffeine, sugar, light, protection from light, actions according to a Program as described herein, and any combinations thereof.

[21] The method according to any of the preceding embodiments, wherein the subject alters a routine or baseline wake time and/or a routine or baseline bed time by at least 2 hours, or by at least 3 hours, or by at least 4 hours, or by at least 5 hours, or by at least 6 hours, or by at least 7 hours, or by at least 8 hours, or by at least 9 hours, or by at least 10 hours, or by at least 11 hours, or by at least 12 hours, or by at least 13 hours, or by at least 14 hours, or by at least 15 hours, or by at least 16 hours, or by at least 17 hours, or by at least 18 hours or more hours; and wherein the one or more adverse effects of jet lag or the one or more adverse effects of a change in sleep-wake timing cycle comprise one or more of insomnia, difficulty falling asleep and/or remaining asleep, difficulty waking at a desired time, stomach discomfort, malaise, soreness, and stiffness.

[22] The method according to any of the preceding embodiments, wherein the method for preventing or reducing one or more adverse effects of jet lag comprises administering to the subject an antioxidant agent, an anti-inflammatory agent, and a circadian shift support agent; or an anti-inflammatory agent, a mitochondrial support agent, and a circadian shift support agent; or an antioxidant agent, an anti-inflammatory agent, a mitochondrial support agent, and a circadian shift support agent.

[23] The method according to any of the preceding embodiments, wherein the method for preventing or reducing one or more adverse effects of a change in sleep-wake timing cycle comprises administering to the subject an anti-inflammatory agent and a circadian shift support agent; or a mitochondrial support agent and a circadian shift support agent; or an anti-inflammatory agent, a mitochondrial support agent and a circadian shift support agent.

[24] The method according to any of the preceding embodiments, wherein the method comprises administering to the subject one or more doses of omega-3 fatty acid during travel day and/or 1 to 2 days after travel day, or on a day in which, or 1 or 2 days after, the subject commences adjusting the routine or baseline sleep-wake timing cycle to a destination sleep-wake timing cycle, wherein the destination sleep-wake timing cycle differs from the routine or baseline sleep-wake timing cycle by at least 2 hours, or by at least 3 hours, or by at least 4 hours, or by at least 5 hours, or by at least 6 hours, or by at least 7 hours, or by at least 8 hours, or by at least 9 hours, or by at least 10 hours, or by at least 11 hours, or by at least 12 hours, or by at least 13 hours, or by at least 14 hours, or by at least 15 hours, or by at least 16 hours, or by at least 17 hours, or by at least 18 hours or more hours.

[25] The method according to any of the preceding embodiments, wherein the method further comprises administering to the subject one or more doses of vitamin C and/or vitamin E.

[26] The method according to any of the preceding embodiments, wherein the method further comprises administering to the subject one or more doses of sugar.

[27] The method according to any of the preceding embodiments, wherein the method further comprises administering to the subject one or more doses of caffeine, melatonin and/or vitamin B12.

[28] The method according to any of the preceding embodiments, wherein the method further comprises instructing the subject to refrain from sleep during travel or on a day in which the subject commences adjusting the routine or baseline sleep-wake timing cycle to the destination sleep-wake timing cycle, and, optionally, one or more days after travel or change in sleep-wake timing cycle, except for one or two program naps, wherein each program nap has a selected length and start time.

[29] The method according to any of the preceding embodiments, wherein the method further comprises exposing the subject to or protecting the subject from bright light, green light, blue light, or any combination thereof for one or more selected periods of time.

[30] A kit for preventing or reducing one or more adverse effects of air travel in a human subject, wherein the kit comprises a dose from about 50 to about 2,000 mg of vitamin C; a dose from about 10 to about 5,000 mg of omega-3 fatty acids; optionally a dose from about 2 to about 450 IU of vitamin E; a pair of glasses that substantially block blue and/or green light; a dose from about 0.1 mg to about 10 mg of melatonin; a dose from about 5 to about 5,000 µg of vitamin B12; optionally one or more of a dose of from about 10 to about 500 mg of magnesium, a dose from about 5 to about 1,000 mg of flavan-3-ol, a dose from about 50 to about 1,000 mg of glutathione, a dose from about 0.1 to about 100 mg of vitamin B6, a dose from about 10 to 500 mg of Co-Enzyme Q10, and a dose from about 1 to about 40 mg of pyrroloquinoline quinone; and instructions for administration of the doses.

[31] The kit according to embodiment 30, wherein each of the doses may be accessed and consumed without unsealing other doses.

[32] The kit according to any of previous embodiment, 30 and 31 wherein each of the doses is contained in a separate package, in a sachet, in a blister pack or in a dosing glass or plastic bottle.

[33] The kit according to any of previous embodiments 30–32, wherein the instructions are accessible via a mobile application.

In view of this disclosure it is noted that the methods can be implemented in keeping with the present teachings. Further, the various components, materials, structures and parameters are included by way of illustration and example only and not in any limiting sense. In view of this disclosure, the present teachings can be implemented in other applications and components, materials, structures and equipment to implement these applications can be determined, while remaining within the scope of the appended claims.

The invention claimed is:

1. A method for-reducing the risks of one or more adverse effects of jet lag associated with a change in sleep-wake timing cycle in a subject in need thereof, wherein the method comprises administering to the subject simultaneously, at different times, or at selected intervals:
methylcobalamin, wherein the methylcobalamin is administered at a dose of from about 50 µg to about 5000 µg;
one or more antioxidant agents comprising vitamin C and one or more flavan-3-ols; and
one or more anti-inflammatory agents comprising one or more omega-3 fatty acids,
wherein the method comprises administering vitamin C and flavan-3-ol(s) 1.5 to 5 hours before commencing air travel.

2. The method of claim 1, wherein the vitamin C is administered at a dose of from about 250 mg to about 1250 mg.

3. The method of claim 1, wherein the vitamin C is administered at a dose of from about 250 mg to about 1250 mg.

4. The method of claim 1, wherein the method comprises administering omega-3 fatty acid(s) 1.5 to 4 hours before commencing air travel.

5. The method of claim 4, wherein the method further comprises administering omega-3 fatty acids(s) at 2–4 hour intervals at least 3 additional times during day of air travel.

6. The method of claim 1, wherein one or both of the vitamin C and omega-3 fatty acid(s) is administered on at least 4 occasions in a 24 hour period, where both are administered together on at least one of these 4 occasions, and where only one of the two is administered on at least one of these 4 occasions.

7. The method of claim 1, wherein the change in sleep-wake timing cycle comprises one or both of (i) a change in routine or baseline wake time of at least 3 hours and (ii) a change in routine or baseline bed time of at least 3 hours.

8. The method of claim 1, wherein the method further comprises administering to the subject simultaneously, at different times, or at selected intervals, one or more circadian shift support agents comprising one or more selected from caffeine, sugar, melatonin, exposure or intentional increase of exposure to light, and protection from light.

9. The method of claim 8, wherein the one or more circadian shift support agents comprise caffeine.

10. The method of claim 8, wherein the one or more circadian shift support agents comprise sugar.

11. The method of claim 8, wherein the one or more circadian shift support agents comprise caffeine and sugar.

12. The method of claim 11, wherein the methylcobalamin, caffeine, and sugar are administered to the subject within 1 hour after waking from a predetermined sleep period, wherein the predetermined sleep period occurs before commencing air travel, during air travel, or after air travel.

13. The method of claim 8, wherein the one or more circadian shift support agents comprise melatonin.

14. The method of claim 13, wherein the melatonin is administered to the subject 1 hour before start of a predetermined sleep period.

15. The method of claim 8, wherein the one or more circadian shift support agents comprise exposure or intentional increase of exposure to light.

16. The method of claim 15, wherein the light is one or more selected from bright light, green light, and blue light, and the exposure or intentional increase of exposure is for one or more selected periods of time.

17. The method of claim 8, wherein the one or more circadian shift support agents comprise protection from light.

18. The method of claim 17, wherein the light is one or more selected from bright light, green light, and blue light, and the protection is for one or more selected periods of time.

19. The method of claim 18, wherein the protection is for two to three hours before the start of a planned sleep period.

20. The method of claim 8, wherein the methylcobalamin, one or more antioxidant agents, one or more anti-inflammatory agents, and one or more circadian shift support agents are administered at different times or at selected intervals, and not only simultaneously.

21. The method of claim 1, wherein the method further comprises administering to the subject simultaneously, at different times, or at selected intervals, one or more mitochondrial support agents comprising one or more selected from ketone salts, ketone esters, medium chain triglycerides, Co-Enzyme Q10, pyrroloquinoline quinone, and vitamin B6.

22. The method of claim 21, wherein the methylcobalamin, one or more antioxidant agents, one or more anti-inflammatory agents, and one or more mitochondrial support agents are administered at different times or at selected intervals, and not only simultaneously.

23. The method of claim 21, wherein the method further comprises administering to the subject simultaneously, at different times, or at selected intervals, one or more circadian shift support agents comprising one or more selected from caffeine, sugar, melatonin, exposure or intentional increase of exposure to light, and protection from light.

24. The method of claim 23, wherein the one or more circadian shift support agents comprise caffeine.

25. The method of claim 23, wherein the one or more circadian shift support agents comprise sugar.

26. The method of claim 23, wherein the one or more circadian shift support agents comprise caffeine and sugar.

27. The method of claim 26, wherein the methylcobalamin, caffeine, and sugar are administered to the subject within 1 hour after waking from a predetermined sleep period, wherein the predetermined sleep period occurs before commencing air travel, during air travel, or after air travel.

28. The method of claim 23, wherein the one or more circadian shift support agents comprise melatonin.

29. The method of claim 23, wherein the one or more circadian shift support agents comprise exposure or intentional increase of exposure to light.

30. The method of claim 29, wherein the light is one or more selected from bright light, green light, and blue light, and the exposure or intentional increase of exposure is for one or more selected periods of time.

31. The method of claim 23, wherein the one or more circadian shift support agents comprise protection from light.

32. The method of claim 31, wherein the light is one or more selected from bright light, green light, and blue light, and the protection is for one or more selected periods of time.

33. The method of claim 32, wherein the protection is for two to three hours before the start of a planned sleep period.

34. The method of claim 23, wherein the methylcobalamin, one or more antioxidant agents, one or more anti-inflammatory agents, one or more circadian shift support agents, and one or more mitochondrial support agents are administered at different times or at selected intervals, and not only simultaneously.

35. A method for reducing the risks of one or more adverse effects of jet lag associated with a change in sleep-wake timing cycle in a subject in need thereof, wherein the method comprises administering to the subject simultaneously, at different times, or at selected intervals:
methylcobalamin, caffeine, and sugar, wherein the methylcobalamin is administered at a dose of from about 50 µg to about 5000 µg, and wherein the methylcobalamin, caffeine, and sugar are administered to the subject within 1 hour after waking from a predetermined sleep period, wherein the predetermined sleep period occurs before commencing air travel, during air travel, or after air travel;
one or more antioxidant agents comprising vitamin C and one or more flavan-3-ols, wherein the vitamin C and flavan-3-ol(s) are administered 1.5 to 5 hours before commencing air travel; and
one or more anti-inflammatory agents comprising one or more omega-3 fatty acids, wherein the omega-3 fatty acid(s) are administered 1.5 to 4 hours before commencing air travel.

36. The method of claim 35, wherein:
(i) vitamin C is administered in a dose of from about 250 mg to about 1250 mg; and
(ii) one or both of the vitamin C and omega-3 fatty acid(s) is administered on at least 4 occasions in a 24 hour period, where both are administered together on at least one of these 4 occasions, and where only one of the two is administered on at least one of these 4 occasions.

37. The method of claim 36, wherein the method further comprises administering melatonin to the subject.

38. The method of claim 37, wherein the melatonin is administered to the subject 1 hour before start of a predetermined sleep period.

39. The method of claim 38, further comprising protection from light, wherein the light is one or more selected from bright light, green light, and blue light, and the exposure or intentional increase of exposure is for two to three hours before the start of a planned sleep period.

40. The method of claim 39, wherein the method further comprises administering to the subject simultaneously, at different times, or at selected intervals, one or more mitochondrial support agents comprising one or more selected from ketone salts, ketone esters, medium chain triglycerides, Co-Enzyme Q10, pyrroloquinoline quinone, and vitamin B6.

* * * * *